United States Patent
Borst et al.

(10) Patent No.: US 6,395,015 B1
(45) Date of Patent: May 28, 2002

(54) TEMPORARY VASCULAR SEAL FOR ANASTOMOSIS

(75) Inventors: Cornelius Borst, Bilthoven; Robin Henricus Heijmen, Wijk Bij Duurstede; Robert Van Dalen, Amersfoort; Paul Frederik Grundeman, Amsterdam; Cornelius Wilhelmus Josef Verlaan, Soest; Henricus Jacobus Mansvelt Beck, Bilthoven; Jules Scheltes, The Hague; Martijn Heikens, Delft, all of (NL)

(73) Assignee: Medtronic Inc., Minneapolis, MN (US)

( * ) Notice: Subject to any disclaimer, the term of this patent is extended or adjusted under 35 U.S.C. 154(b) by 0 days.

(21) Appl. No.: 09/463,746

(22) PCT Filed: Jul. 29, 1998

(86) PCT No.: PCT/NL98/00430

§ 371 (c)(1),
(2), (4) Date: Mar. 22, 2000

(87) PCT Pub. No.: WO99/08603

PCT Pub. Date: Feb. 25, 1999

(30) Foreign Application Priority Data

Jul. 31, 1997 (EP) ............................................. 97202393
Mar. 18, 1998 (EP) ............................................. 98200847

(51) Int. Cl.$^7$ ............................................. A61B 17/08
(52) U.S. Cl. ........................ 606/213; 606/215; 606/153
(58) Field of Search ................................. 606/151, 153, 606/157, 158, 194, 213, 215, 232; 604/96.01, 102.07

(56) References Cited

U.S. PATENT DOCUMENTS

| | | | | |
|---|---|---|---|---|
| 4,852,568 A | * | 8/1989 | Kensey | ........................ 606/213 |
| 5,108,421 A | * | 4/1992 | Fowler | ........................ 606/213 |
| 5,258,000 A | * | 11/1993 | Gianturco | ........................ 606/151 |
| 5,312,435 A | * | 5/1994 | Nash et al. | ........................ 606/213 |
| 5,383,897 A | | 1/1995 | Wholey | |
| 5,413,571 A | * | 5/1995 | Katsaros et al. | ........................ 606/213 |
| 5,545,178 A | * | 8/1996 | Kensey et al. | ........................ 606/213 |
| 5,620,461 A | | 4/1997 | Muijs Van De Moer et al. | |

FOREIGN PATENT DOCUMENTS

| | | |
|---|---|---|
| DE | 297 01 981 | 5/1997 |
| EP | 0 791 332 | 8/1997 |
| WO | WO 95/17128 | 6/1995 |

* cited by examiner

Primary Examiner—David O. Reip
Assistant Examiner—Julian W. Woo
(74) Attorney, Agent, or Firm—Young & Thompson

(57) ABSTRACT

A temporary intravascular arteriotomy seal for insertion into and retrieval from a blood vessel through an opening in the wall of the vessel. The seal comprises a thin flexible sheet material. According to one embodiment, in an untensioned state, the seal is curved and foldable in the width direction. It is adapted to be folded in the width direction upon exertion for a force on the gripping element directed in the length direction, and upon contacting of the sheet material by the sides of the opening in the vessel wall. By use of the sealing device, arterial by-pass grafting in a briefly-occlusive or non-occlusive end-to-side or side-to-side anastomosis technique is possible with virtually no obstruction to flow, little endothelial denudation and otherwise no wall damage by the intravascular device, and without blocking of side branches. A further embodiment of a device according to the present invention is characterized in that the gripping element is formed by a supply duct which ends in an opening in the flexible sheet material for administration of substances to the supply duct into a blood vessel for rescue arterial perfusion purposes. Optionally, the seal may be inflatable.

30 Claims, 9 Drawing Sheets

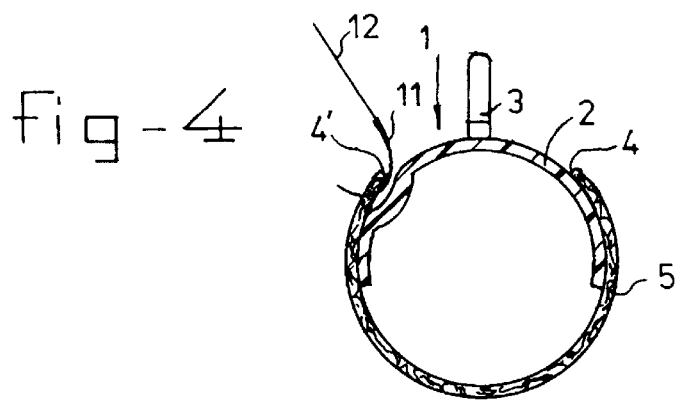
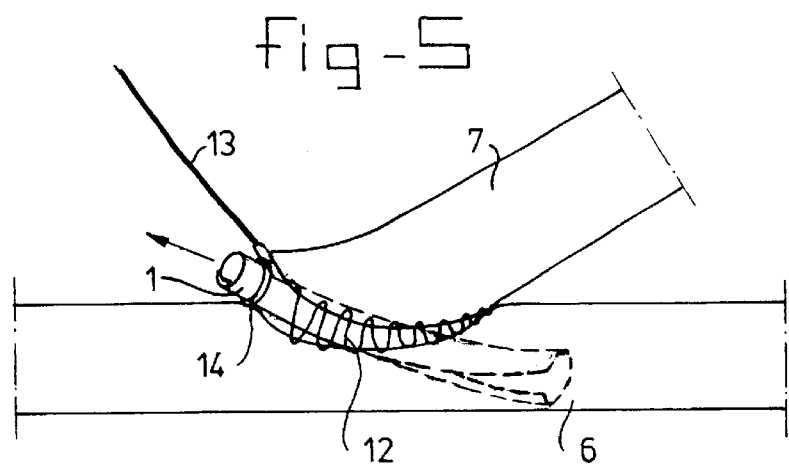
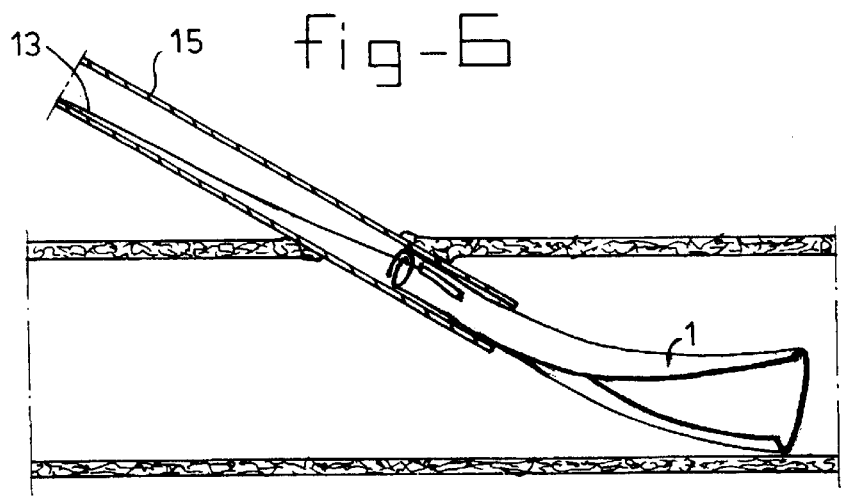

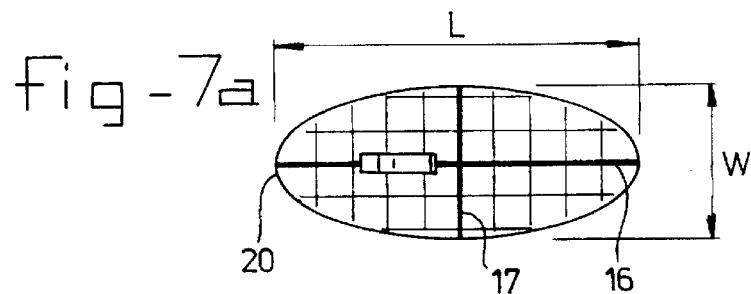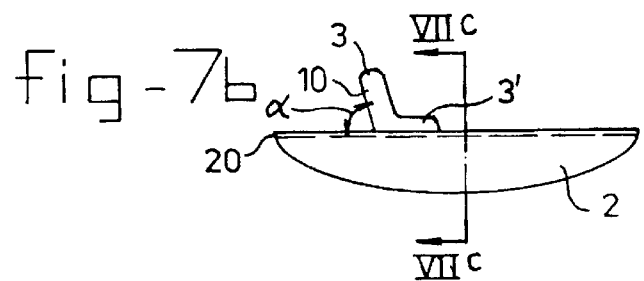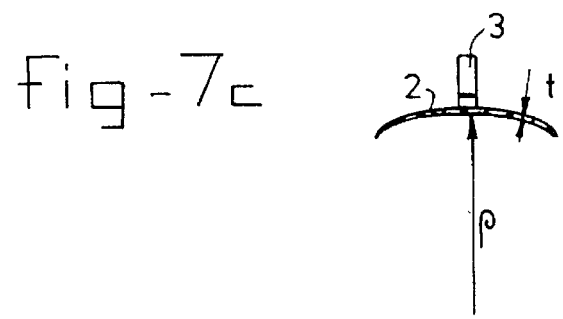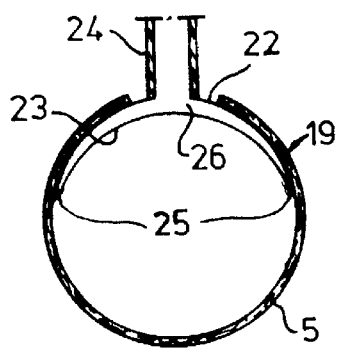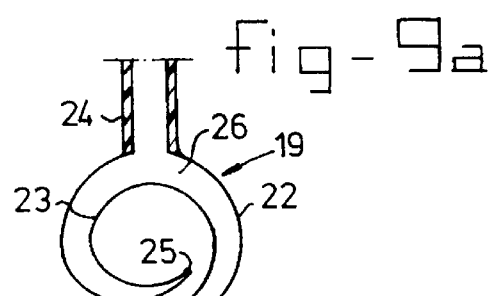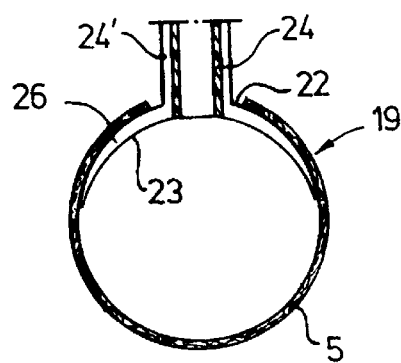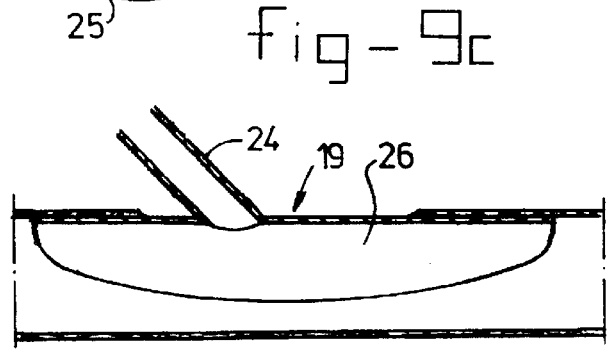

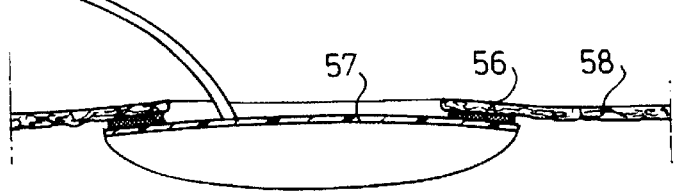
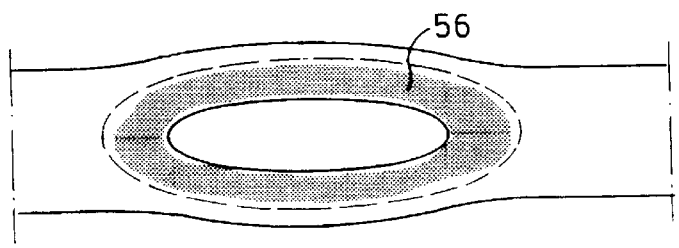
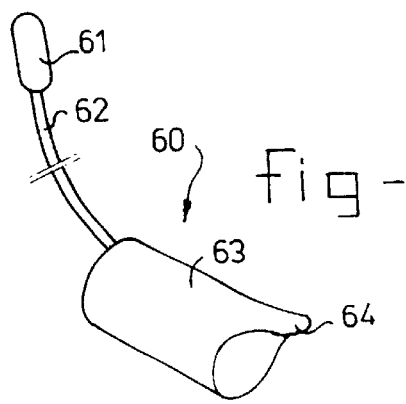
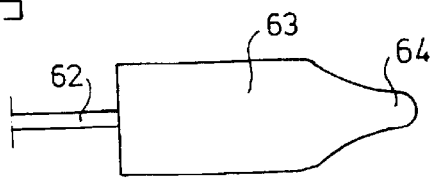

TEMPORARY VASCULAR SEAL FOR ANASTOMOSIS

BACKGROUND OF THE INVENTION

The invention relates to a medical device for insertion into a blood vessel through an opening in the wall of said blood vessel, the device comprising a flexible sheet material having a length dimension and a width dimension, the sheet material being foldable in the width direction for placing the sheet material into an insertion configuration and the sheet material being unfoldable to assume a sealing configuration inside the blood vessel for a traumatically contacting the blood vessel wall in a sealing manners the sheet material in the sealing configuration extending along an open contour, partly covering the vessel wall, the device further comprising a gripping element on its outer surface.

From WO 90/14796, an occlusion assembly for sealing puncture openings in blood vessels is described. After puncturing a blood vessel with a needle and introducer sheath and subsequent withdrawal of the needle, the known occlusion device can be inserted into the vessel via the introducer sheath. The known occlusion device comprises a flexible sheet material which is attached to a retaining element such as a thread. In the blood vessel, it unfolds to have a surface area which is larger than the surface area of the puncture opening to be occluded. Subsequently the introducer sheath is removed out of the opening in the vessel and by pulling the retaining thread, the sheet material of the occlusion element will come to lie against the inside of the blood vessel wall. Thereafter, a retainer ring is placed around the thread and engages with the outer surface of the blood vessel for a fixed positioning of the occluding device. The flexible sheet, the thread and the retainer ring are made of bioabsorbable material such that it is ensured that after the opening in the blood vessel has been occluded, these parts will disappear, for example after a few weeks.

SUMMARY OF THE INVENTION

It is an object of the present invention to provide a vascular surgery device and method which enables formation of a connection (anastomosis) between a bypass graft and a donor or recipient blood vessel with little or no interruption of the blood flow in the donor or recipient vessel. It is an object of the present invention to provide a vascular surgery device which can be used for instance in coronary bypass surgery, preferably on the beating hart, as well as in peripheral bypass surgery, cerebral bypass surgery and plastic and reconstructive vascular surgery. It is a further object of the present invention to provide a vascular surgery device which can be easily and effectively applied and retrieved with a minimum of trauma to the blood vessel and within a very short period of time, preferably within about one minute.

Thereto the medical device according to the present invention is characterised in that the flexible sheet material in an untensioned state is curved in the width direction. After completion of the anastomosis, the device according to the invention can be easily and reliably retrieved from the recipient vessel as the sheet material is predisposed by its flexibility and its pre-formed curvature to be folded in the width direction upon exertion of a pulling force on the gripping element, directed generally in the length direction of the device. Upon retrieval the sheet material is folded when it is contacted by the sides of the opening in the vessel wall.

The present invention provides an intravascular arteriotomy seal which can be easily inserted into and retrieved from a donor or recipient vessel. During insertion into a recipient artery, occlusion of the artery is required only for a brief moment or is not required at all when intravascular pressure is low. When the seal according to the invention is in place, the blood flow in the opened artery can be resumed and the distal end of the bypass graft can be grafted onto the opening of the recipient vessel without leakage of blood along the seal. Prior to completion of the bonding, such as by tightening (securing) the sutures which connect the bypass graft to the recipient vessel, the sheet material of the device according to the present invention can be withdrawn from the opening in the recipient vessel wherein the device will easily bend in the width direction by contact with the sides of the opening in the vessel wall, due to its flexibility and preformed curvature in the width direction. Thereafter, the sutures can be tightened and the grafting can be completed. With the device according to the present invention only a very short or no occlusion of the blood vessel upon insertion or retrieval is required. Once properly positioned, the seal according to the invention provides a bloodless arteriotomy for precise (microsurgical) anastomosis suturing without interfering with recipient artery blood flow, with minimal damage to the wall of the vessel and without blocking of any side branches in the vessel. The seal according to the invention will be particularly useful for coronary artery bypass grafting on the beating heart, such as for instance described in co-pending patent application WO 97/10753 in the name of the applicant. Because the sheet material of the seal according to the present invention has a preformed curvature in the width direction, the material will have a natural tendency to fold easily in the width direction. Hereby the device can be easily retrieved through the insertion opening by pulling, contrary to the prior art puncture hole occlusion device that is described in WO 97/14796, which is maintained in its unfolded position after insertion into a blood vessel.

Bypass Grafting

To provide adequate blood supply to an organ or tissue with impaired blood supply, the end of an extra vessel (bypass graft) is connected end-to-side or side-to-side to the recipient artery downstream of the obstruction in the recipient artery.

To establish this connection, i.e. the distal anastomosis, blood flow in the recipient artery is interrupted by, for example, temporary ligation or clamping of the artery proximal and distal of the connection site. Once the blood flow is interrupted, the recipient artery is opened (arteriotomy). Next, the exit (distal end) of the bypass graft is connected by suturing (or other bonding method) to the recipient artery. This is achieved by suturing the inside of the bypass graft to the inside of the recipient artery. The rationale of this precise anastomosis suturing is that the inner lining of the vessels (the endothelial layer) is anti-thrombogenic, whereas the outer layer is highly thrombogenic. Thrombosis at the transition of donor to recipient vessel reduces the cross-sectional area of the lumen at the anastomosis and hence jeopardizes the quality of the distal anastomosis. Narrowing (stenosis) of the anastomosis limits the maximum blood flow through the bypass graft.

In a proximal anastomosis, the entrance (proximal end) of the bypass graft needs to be connected to an artery which serves as pressure source of oxygenated blood. If a natural artery can serve as bypass graft, like e.g. the internal mammary artery in coronary artery bypass grafting, only the distal anastomosis needs to be made. Sometimes, however, the internal mammary artery is used as free graft or the radial artery is used as arterial conduit and a proximal anastomosis has to be made. Venous bypass grafts always require a proximal anastomosis, because their transformation to an arterial conduit requires connection to a source of arterial blood. Similar to suturing the distal anastomosis of the bypass graft, suturing the proximal anastomosis requires interruption of the source blood flow in the vicinity of the proximal anastomosis site.

Interruption of Blood Flow in Vascular Surgery: Adverse Effects

Currently, all vascular surgery is performed during interrupted blood flow in the vicinity of the anastomosis, because suturing (or otherwise bonding the vessel edges) requires a bloodless surgical field for proper exposure of the vessel edges. The bloodless field, however, is obtained at a price.

Temporary interruption of blood flow has potentially a number of adverse effects. First, interruption of existing residual flow through a high grade stenosis or, when the artery is proximally totally occluded, interruption of collateral flow to the end-organ may impair its function (ischemic dysfunction). Second, it my jeopardize the end-organ's cellular integrity (ischemic injury). Third, re-establishment of blood flow after cessation of flow may lead to reperfusion injury and dysfunction. Fourth, during the period of completely interrupted flow, in ischemic tissues noxious metabolites accumulate. The abrupt release into the circulation of accumulated noxious metabolites from the reperfused area may cause adverse effects elsewhere.

Vascular surgeons limit the period of flow interruption as much as possible by performing bypass surgery as fast as possible. This requires (a) a still surgical field, (b) absence of blood which obscures the vessel edges, and (c) experience, concentration and manual dexterity. The distal anastomosis requires meticulous placement of the needle into the edge of the recipient artery entrance (arteriotomy). If the stitch is too close to the edge, there is the risk of wall tissue tearing by the suture wire. If the stitch is too far from the edge, there is the risk of creating a tissue flap in the lumen of the anastomosis with subsequent risk of suture line mural thrombosis and suboptimal anastomosis quality.

The present invention obviates the need to interrupt flow in the recipient artery or limits it to less than about 2 minutes, a period which is not expected to lead to adverse effects.

Coronary Bypass Grafting

Recently, coronary artery bypass grafting on the beating heart has regained interest. Coronary motion can now be restrained adequately with a mechanical stabilization device, as described in WO 97/10753, in the name of applicant. Interruption of the coronary flow, however, in the segment of the recipient artery to be grafted may result in regional myocardial ischemia with ischemic ecg changes, loss of regional contractile function and hence, impaired cardiac pump function. Ischemia may induce conduction disturbances. In addition, inhomogeneous perfusion of the myocardium may create vulnerability to arrhythmias. Changes in rate or rhythm may impair pump function. Reperfusion may cause myocardial cell injury ("reperfusion injury") and induce ventricular fibrillation which causes immediate cessation of all pumping action. However, due to usually well established collateral circulation in patients that require coronary bypass grafting for stable angina, flow interruption for 10–20 minutes is remarkably well tolerated without plasma CPK-MB rise indicative of myocardial cell death. In unstable angina, in contrast, adequate collateral circulation is likely to be absent and coronary flow interruption during emergency coronary surgery on the beating heart may further damage the jeopardized myocardium.

Collateral Coronary Flow

In the normal heart, perforating side branches of the epicardial coronary artery feed the underlying myocardium. In case of a proximal occlusion, there is (limited) flow in these perforating branches, albeit in the reverse direction (collateral flow). The sources of the collateral flow are tiny interconnections with nearby unobstructed branches of the arterial coronary tree. In patients with stable angina pectoris the collateral flow usually has sufficient capacity to provide the flow through the main epicardial conduit needed for the heart during resting conditions. During exercise, however, blood supply becomes insufficient and the patient experiences cardiac ischemia (angina pectoris). Since the lesion progression from flow limiting to totally occlusive atherosclerotic obstruction takes many years, collateral circulation has had ample time to develop by expanding the originally minute interconnections between branches of the coronary tree.

In elective coronary bypass grafting for stable angina owing to a proximal coronary occlusion, the well developed collateral circulation generally allows clamping and isolating of the mid-segment of the coronary artery for creation of the distal bypass connection. However, the consequences of temporary occlusion of the recipient artery proximal and distal of the anastomosis site are unpredictable, because very small arteries cannot be visualized pre-operatively by angiography. Distal clamping of a proximally occluded artery may produce myocardial ischemia in the distal perfusion area, because collateral flow in the epicardial conduit is blocked in the antegrade direction. In addition, clamping or ligating the coronary artery may also block retrograde collateral flow in the epicardial conduit from a more distal side branch to a more proximal side branch which supplies a region which happens to lack adequate collateral flow. Sometimes, the coronary flow interruption is not tolerated and the pumping function of the heart deteriorates. One remedy is to restore the blood flow and convert the procedure to conventional coronary bypass grafting using the heart lung machine. If the coronary artery has already been opened, emergency conversion becomes necessary. Another remedy is to insert an intra-coronary shunt cannula. The present invention prevents ischemic problems and hence, obviates stand-by of the heart lung machine.

Dry Surgical Field

To perform precise coronary bypass surgery, a good view of the arteriotomy edges is required. The presence of blood hampers suturing. Ample collateral flow via perforating branches that happen to be located in the occluded coronary segment produces retrograde flow that wells up in the arteriotomy, obscures its edges and jeopardizes the quality of the anastomosis. The present invention restores the dry surgical field and allows conventional anastomosis suturing without leakage of blood owing to the flexibility of the sealing sheet. In the standard, conventional bypass surgery, the heart is arrested by perfusion of the coronary arteries with, in general, a cold cardioplegic crystalline solution which provides a perfectly clear view on the arteriotomy edges. However, when for example the heart muscle is protected by retrograde blood cardioplegia, the same obscuring effect of blood hampers the anastomosis suturing and the present invention may provide a dry surgical field in spite of the blood cardioplegia. Thus, a useful additional benefit of the temporary luminal arteriotomy seal is the creation of a dry surgical field with unimpaired view on the arteriotomy edges for meticulate anastomosis suturing.

Obstruction to Flow

With the intravascular seal and method of using said seal according to the present invention, which seal may for instance be made of polyurethane of a thickness of about 0.2 mm, a minimal or no decrease in cross-sectional area of the recipient artery lumen is achieved, resulting in a minimal or no obstruction to flow.

Vessel Wall Injury

The major concern with any device inserted in an artery is its potential for wall injury, because intra-arterial injury to the wall may lead to local luminal narrowing due to acute mural thrombosis and/or formation of intimal hyperplasia (scar tissue). As the device according to the present invention will only contact a part of the vessel wall circumference, endothelial damage by the intravascular device of the present invention is minimized. Furthermore, if it has damaged or removed endothelium, re-endothelialization is accelerated owing to the presence of undisturbed endothelium at the opposite side of the arteriotomy. In addition, by only covering a limited part of the inner circumference of the vessel with the seal according to the invention, the entrance to side branches remains open during bypass grafting.

Proximal Anastomosis

One major objective of coronary bypass graft (CABG) surgery on the beating heart is to avoid adverse cerebral effects which occur in 6% of cases. These serious adverse effects are attributed for about 50% to relatively large emboli generated by manipulation of the ascending aorta and for about 50% to relatively small emboli generated by the use of the heart-lung machine, in combination with low arterial pressure.

In the CABG patient, the ascending aorta is usually atherosclerotic as well. Any manipulation of the atherosclerotic ascending aorta may dislodge particulate, atherosclerotic or thrombotic emboli from the aortic wall. These emboli may block the (micro)circulation anywhere in the body, but if an embolus follows the bloodstream to the brain, the consequences may be particularly serious.

In conventional CABG using the heart-lung machine and cardioplegic cardiac arrest, the ascending aorta has to be cross-clamped. Off-pump, beating heart CABG obviates the need to cross-clamp the ascending aorta. Currently, however, virtually all vein grafts are connected at their proximal end to the ascending aorta as source of pressurized oxygenated blood. Each time a side clamp is applied to create a dry surgical field, there is the risk of dislodging particulate emboli.

A slight modification of the earlier described arteriotomy seal according to the present invention, to be used for the distal anastomosis, will obviate the need to apply a side-clamp on the (ascending) aorta for creating the proximal anastomosis of a vein graft or a free arterial graft.

In addition, side-clamping the ascending aorta in an off-pump beating heart CABG patient will locally reduce the cross-sectional luminal area, and hence, will increase resistance to flow. Both the ensuing increased arterial pressure in the ascending aorta proximal to the side-clamp (increased afterload for the left ventricle) and the decreased arterial blood pressure beyond the side-clamp (decreased perfusion pressure for the brain and other tissues) are unwanted side-effects.

Thus, obviating the need for the aortic side-clamp is useful both in off-pump CABG and in conventional CABG using the heart-lung machine.

Conceptually, the sealing device for the proximal anastomosis on the ascending aorta is the same as for the distal anastomosis, but the embodiment is slightly different. First, the hole in the aorta is not created by a longitudinal incision, but by punching a round hole (3–4 mm in diameter). Second, the dimensions of the seal conform to the ascending aorta with an internal diameter 25–30 mm and wall thickness 15 mm. Thus, the umbilical cord/inflation channel cannula inserts in the middle of the seal. Fourth, the seal is oval or round. Fifth, the inflatable embodiment may be a torus as well ("dough-nut").

Method. After punching the hole, the sealing device is inserted in the hole (and inflated). Traction on the umbilical cord/inflation cannula may be needed to obtain proper sealing without leakage.

Similar to the distal anastomosis, the aortic sealing device effectively seals the punch hole and permits conventional anastomosis suturing owing to the seal giving way to the needle with little or no leakage. Little leakage will pose no problem, because a clear field is easily obtained by flushing with saline. Similar to the distal anastomosis, the seal is deflated and retrieved after all stitches have been placed but prior to tightening the running suture. The umbilical cord/inflation cannula has a stopping plate or ring/syringe connector to prevent loosing the sealing device within the aorta.

The intravascular seal according to the present invention comprises in one embodiment a relatively short gripping device on the outer surface thereof. The gripping device may be formed by a notch, placed at a specific angle with respect to the outer surface of the seal. With the notch, which may for instance be of a thickness of 0.5 mm and of a height of about 1 mm, the seal can be manipulated during insertion for positioning the seal correctly inside the vessel, and during retrieval.

For properly orienting the seal, an upstanding ridge can be provided on the outer surface within the boundary of the arteriotomy such that the seal may be rotated inside the vessel. Orientation markings, for instance a grid structure may be applied on the outer surface for proper positioning. To minimize the risk of spontaneous inadvertent expulsion of the seal, the stiffness of the flexible sheet material can be greater in the length direction than in the width direction, for example by a midline thickening (longitudinal ridge at luminal side of flexible sheet).

A further embodiment of the device according to the present invention comprises an inflatable body, for instance two membranes that are sealingly connected along their perimeter and a supply duct for supply of a fluid into the space between the membranes for inflating and deflating the sealing device. The luminal membrane is made of a stiffer material to keep the space between both membranes exceedingly small. In this way, the expansion of the device in the width direction can take place by inflation. By deflating the seal, and for instance creating a slight vacuum inside, the dimensions of the seal can be reduced significantly for easy insertion into and retrieval from the vessel.

In another embodiment of the arteriotomy seal according to the invention, the gripping element is formed by a supply duct which ends in an opening in the flexible sheet material for administration of substances through the supply duct into the recipient blood vessel. This device is particularly suitable for instance for performing a rescue blood perfusion during emergency coronary bypass grafting. The rescue blood perfusion pressure should not exceed normal intra-coronary pressure in order to avoid inadvertent expulsion of the device. The perfusion seal may be used in a non-rescue situation when contractile function of the distal myocardium is marginal.

As the seal according to the present invention is retrieved from the vessel the material is non biodegradable which allows for a large choice of suitable, non biodegradable materials such as for instance a polyurethane material, or other materials from which commercially available balloon catheters are manufactured such as available from Medtronic, Minn., USA; Research Medical Vascular, Research Medical, Inc. Midvale, Utah, USA.

The seal according to the present invention was evaluated in a porcine carotid artery (internal diameter 3.5 mm) bypass graft model. In 16 consecutive pigs (32 anastomoses), the seal insertion time was about 20 seconds. The retrieval time was about 5 seconds. Together with the time required for making the arteriotomy and securing the running suture, respectively, median occlusion time upon insertion or retrieval was about 90 seconds. Microsurgical suturing was performed without leakage of the seal and with unimpeded flow. Throughout the anastomosis, no more than one third of the inner circumference of the recipient artery at the anastomosis showed absence of endothelial cells after two days. No medial necrosis was observed. After four weeks, intimal hyperplasia at the sutureline was not significantly different from conventionally sutured anastomoses.

Application of the seal during left internal mammary artery bypass grafting to the left anterior descending coronary artery (internal diameter, 2 mm) on the beating heart was successful in the first 7 additional pigs.

BRIEF DESCRIPTION OF THE DRAWINGS

The arteriotomy seal according to the present invention and the method of connecting two blood vessels using said seal will be described in detail with reference to the accompanying drawings.

In the drawings:

FIG. 4 shows the functioning of the sealing device during suturing along the edge of the opening in the vessel wall, FIG. 5 shows a schematic perspective view of the retrieval of the seal according to the present invention, FIG. 6 shows a schematic side view of the insertion of the seal according to the invention via an introducer sheath, FIGS. 7a to 7c respectively show a top view, a sideview and a cross-sectional view along the line c—c in FIG. 7b of the seal according to the present invention, FIG. 8 shows a transverse cross-sectional view of a sealing device according to the present invention, comprising a stopping plate or ring, FIGS. 9a, 9b and 9c respectively show a transverse cross-sectional view and an axial cross-sectional view of an inflatable embodiment of the seal according to the present invention in respectively an uninflated and in an inflated state, whereas

FIGS. 14a and 14b show a cross-sectional view and a plan view of a sealing device having a flexible sealing material connected along a closed contour of the upper part thereof, FIGS. 15a and 15b show a schematic perspective view and a plan view of an introducer for introducing a sealing device according to the present invention.

DESCRIPTION OF THE PREFERRED EMBODIMENTS

Figure 1:
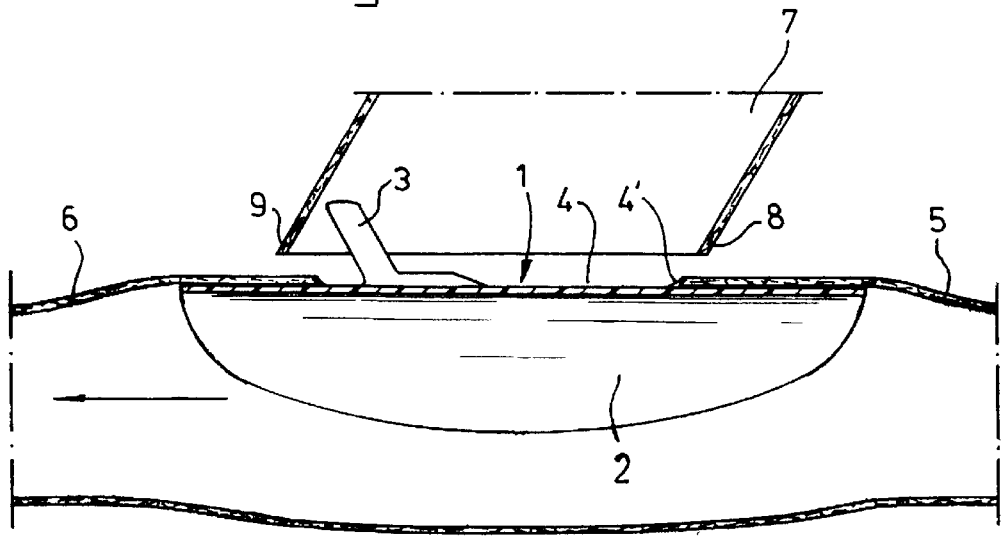
FIG. 1 shows an axial cross-sectional view of a recipient vessel comprising the sealing device according to the present invention.
Figure 2:
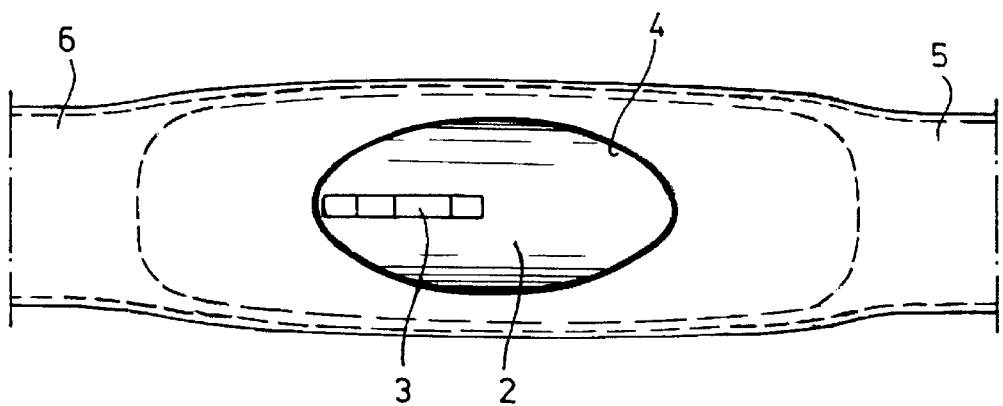
FIG. 2 shows a plan view of the device according to FIG. 1.
Figure 3:
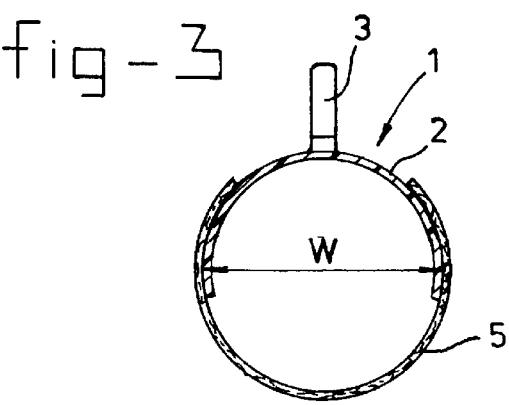
FIG. 3 shows a transverse cross-sectional view of the vessel of FIG. 1.

FIG. 1 shows the medical device, or temporary luminal arteriotomy seal 1 according to the present invention, which is comprised of a flexible sheet material 2 having a gripping element 3 ("shark fin") on its outer surface. The seal 1 is introduced into a recipient vessel 6 through an opening 4 (arteriotomy) in the vessel wall 5. The seal 1 provides a leakage tight occlusion of the opening 4, allowing attachment of the donor vessel 7 around the edges 4' of the opening 4 with a heel 8 and toe 9 as indicated. As is shown in FIG. 2, a linear incision in the vessel wall will due to the tension in the elastic wall open into an elliptical opening 4. The sheet material of the seal 1 is sufficiently flexible such that its width dimensions, which are indicated as W in FIG. 3, can be made sufficiently small by folding to fit through opening 4 upon insertion and upon retrieval. After introduction into the vessel, the blood pressure will sealingly engage of the flexible sheet material 2 with the inside of the wall of the vessel in the vicinity of the opening 4. Once in the proper place, the transmural pressure in the artery will keep the extremely thin seal skin neatly apposed to the inner arterial wall, thereby sealing the arteriotomy, even in the case of (atherosclerotic) luminal wall surface irregularities. At the positioning of the opening 4, the cross-sectional area of the vessel will slightly increase due to expansion of the vessel after making the incision, such that the introduction of the thin seal does not impede the blood flow through the vessel.

As can be seen in FIG. 4, the flexible sheet material 2 will flex and give way when a needle 11 is stuck from inside to outside through the edge 4' of the walls of the vessel near the opening 4 while still maintaining a liquid tight barrier preventing blood from exiting from the vessel through opening 4.

As shown in FIG. 5, the seal 1 is removed from the vessel when a suture or sutures 12 around the perimeter of the opening 4 has been completed, but not tightened. The seal 1 is pulled out of the vessel by means of shark fin 3 grasped by a forceps through the loose loops of the suture 12, which thereafter is tightened to secure the bypass graft 7 to the recipient vessel 6. Upon insertion (as well as upon retrieval) a sleeve 14 may be used around the seal 1, for easy insertion (and retrieval).

As shown in FIG. 6, the seal 1 may be introduced into the vessel 6 by means of a hollow sheath 15, in a manner which is well-known in itself, and may be positioned and withdrawn by means of a thread 13.

FIG. 7a shows a preferred embodiment of the intravascular seal according to the present invention having along its longitudinal axis 16 a length dimension, L, and a dimension in the width direction, W, along the transverse centre line 17. In the porcine carotid artery (internal diameter, 3.5 mm), a 5 mm longitudinal arteriotomy requires approximately L=12 mm and W=7 mm for proper sealing. In the porcine left anterior descending coronary artery (internal diameter, 2.0 mm), a 4 mm arteriotomy requires approximately L=9 mm and W=6 mm.

Along the longitudinal centre line 16, within the boundaries of the arteriotomy a ridge may be provided for manipulation purposes. As can be seen in FIG. 7b, the gripping element 3 is placed at an angle a directed towards the toe of about 60 degrees with respect to the outer surface of the sheet material 2. The height of the gripping device 3 is about 1 mm. The gripping element 3 is positioned eccentrically towards the toe of the anastomosis with its back edge 10 at a distance of about 2–4 mm from the edge 20 of the sheet material 1. A ridge 3' is provided for manipulation (rotation) of the seal 1 inside a vessel. As can be seen in FIG. 7c, the thickness t of the sheet material is about 0.2 mm and the sheet material comprises a predisposed radius of curvature ρ. By providing a preformed curvature, the flexible sheet material 1 will easily fold in the width direction W which allows for easy insertion and retrieval through an opening in the vessel wall. On the other hand, the flexible sheet material has a natural tendency to unfold and appose the vessel wall adjacent to the opening 4.

FIG 8 shows a round or oval sealing device 1 particularly suitable for use in the proximal anastomosis. The flexible sheet material 2 comprises a long, flexible stem 3' (umbilical cord) which is provided with a stopping plate 3". De stopping plate 3" prevents the sealing device from inadvertently entering into the blood vessel.

Figure 9:
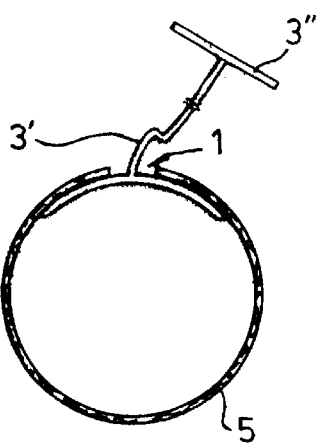
FIG. 9d shows a transverse cross-sectional view of an inflatable device of the double lumen type.

FIGS. 9a shows an inflatable seal 19 according to a second embodiment of the present invention in its partly deflated state. The inflatable seal 19 comprises an inflatable element 26 having two membranes 22, 23, which are sealed along their perimeter 25. The membranes 22, 23 are connected to a supply duct 24 by which a fluid, for instance saline, can be introduced between the membranes 22, 23. Hereby the inflatable element 26 of the seal 19 assumes its inflated position as shown in FIG. 9b. The membrane 22 is relatively compliant and apposes the wall 5. Luminal membrane 23 is relatively stiff. In the inflate state, the distance between membrane 22 and membrane 23 is minimal to create a minimal cross-sectional area (obstruction to flow). In a completely deflated state (active suction), membranes 22 and 23 touch each other. By their pre-formed moulding, deflation results in resumption of the original folded state which by its small size allows easy insertion and retrieval. FIG. 9c shows an axial cross-sectional view of the device 19 of FIGS. 9a and 9b. Depending on the inflation pressure the inflatable seal adjusts to the radius of curvature of the artery and seals the arteriotomy. Similar to the non-inflatable device, its cannula and balloon skin material are non-thrombogenic (possibly heparin or other anti-coagulation compound coated), atraumatic and possibly hydrophyllic (c.f. glide wire). The balloon skin 22 is compliant, such that the suture needle can follow its regular course from inside to outside without producing a leak. The balloon skin gives way to the needle if the needle point is not positioned perpendicularly to the inflatable seal's skin.

With the ultrathin skin and limited size of the inflatable seal 19, three objectives are satisfied: (1) minimal decrease in cross-sectional area of the recipient artery lumen and hence, minimal obstruction to flow; (2) minimal wall damage by the intra-vascular device; (3) by not covering the entire circumference as by e.g. an intra-coronary cannula shunt, the entrance to side branches is not blocked. The absence of circumferential injury may accelerate re-endothelialization by spread of endothelial cells from the side of the artery opposite to the arteriotomy, rather than from minute side branches (vasa vasorum) and the proximal and distal, non-occluded segments. The former is a shorter distance. Smooth muscle cells are not injured. In the pig, the minimal endothelial injury causes no mural thrombus formation. The minimal intimal hyperplasia response is similar to healing after conventional suturing.

The lumen of the inflatable seal 19 is minimal to reduce the arterial lumen least. The seal 19 has a preformed shape which fits the size of the artery. In the deflated state, the seal takes the shape depicted in FIG. 9a. The luminal side of the seal is made of a balloon skin which has the property that it takes on the depicted shape. The curling should be as tight as possible to obtain the lowest profile in cross-section. The seal is inflated by saline. The inflation pressure is monitored. Inflation pressure is determined empirically. Inflating the seal 19 will de-curl the seal. A further increase in inflation pressure will stretch it. Little inflation pressure suffices to keep the seal in its proper shape and position.

By increasing the pressure in the inflatable seal, it extends more laterally and it becomes more stiff. In this condition, more traction can be exerted on its attachment, if needed, before it slips out of the arteriotomy. It might be useful, for example, to exert some traction to lift the artery a little out of its bed. This will add to the safety margin of the device as described in WO 97/10753 with respect to inadvertent release of the epicardium by the Octopus™ Tissue Stabilizer.

By decreasing the pressure, the seal takes on its more deflated, curled shape and becomes less stiff and may follow more the possibly irregular inner surface of the atherosclerotic artery. With very little inflation pressure it will probably seal perfectly due to the transmural pressure in the artery, once it has been positioned properly.

FIG. 9d shows an inflatable seal 19 wherein the membrane 22 extends upwardly along the supply duct 24, to form a so-called double lumen cannula having two ducts 24, 24'. The inflatable element 26 of the seal 19 can be inflated by means of duct 24'. Via central duct 24 blood perfusion can be carried out or drugs can be delivered to the vessel. The double lumen cannula 24, 24' itself is also used as a cord to insert, manipulate and retrieve the seal.

The principle depicted in FIGS. 9a–9d implies that one seal may fit different sizes arteries within a certain range, e.g. for coronary artery bypass grafting. In an artery which is relatively small in relation to the seal, however, the device may become flow limiting. For femoral artery bypass grafting, obviously a larger size seal is required.

The inflatable seal may be positioned in either two ways: (1) through the arteriotomy, or (2) via an introducer sheath that has been positioned in the recipient artery. The second method is similar to inserting a catheter into an artery via an introducer. The introducer with needle is inserted into the lumen of the recipient artery. The needle is withdrawn and the seal is inserted in deflated and low profile state like a balloon catheter into the lumen. Next, the introducer is removed over the supply cannula of the seal.

When the seal has been inserted through a sheath, after inflation the puncture site can be enlarged to a full size arteriotomy by hooked scissors, taking care not to puncture the balloon skin of the seal. Again, the seal will give way to the lower jaw of the scissors without causing a leak.

The supply cannula of the seal has two and possibly four functions: (1) a cord to insert, manipulate and retrieve the seal; (2) inflation/deflation channel of the seal; (3) channel for local drug delivery; and (4) rescue blood perfusion.

If the inflatable element 26 of the seal 19 is made of balloon material with microscopic pores, the seal can function as local drug delivery device. For example, local heparin delivery reduces the risk of clot formation and inhibits local intimal hyperplasia as vessel wall repair response to vascular surgery injury. The local delivery of heparin may reduce or even abolish the need for anti-coagulation during anastomosis suturing. Obviating the need for systemic anti-platelet therapy and anticoagulation will contribute to reducing bleeding problems.

After deflation of the seal, it resumes its low profile shape which facilitates its removal through a small residual opening in the anastomosis. At this stage, all stitches have been made, but the running suture wire has not yet been fastened. During retrieval and removal, some bleeding will occur which will stop as soon as the suture wire loops are picked up and the wire is tied.

Figure 10:
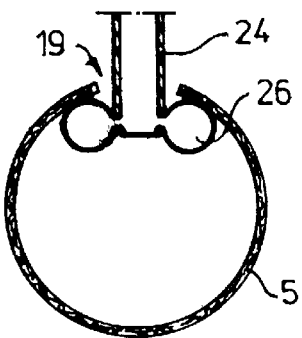
FIG. 10 shows a further embodiment of an inflatable sealing device according to the present invention.

FIG. 10 shows an embodiment particularly suitable for the proximal anastomosis on the aorta, in which the sealing device 19 comprises a dough-nut-shaped inflatable element 26.

Figure 11:
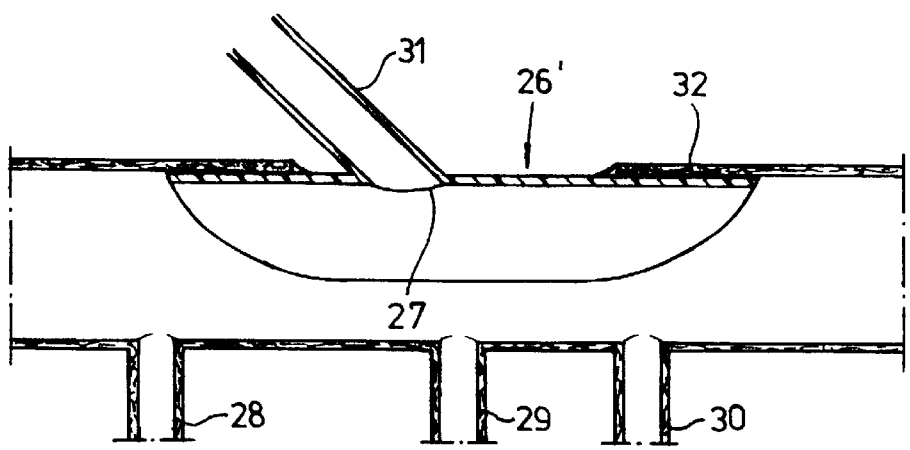
FIG. 11 shows an axial cross-sectional view of a device according to the present invention suitable for emergency perfusion.

In FIG. 11, a non-inflatable sealing device 26' for use in rescue arterial perfusion is shown. In this embodiment similar to FIG. 1, the flexible sheet material 32 comprises an opening 27 which is in fluid communication with a supply cannula or duct 31 for blood supply. The supply cannula 31 can be fed either directly from the arterial tree or via a pump. The supply cannula of the seal has three functions: (1) a cord to insert, manipulate and retrieve the seal; (2) channel for blood perfusion; (3) channel for delivery of drugs. By use of this seal 26', according to the present invention all side branches 28 and 29 and 30 can also be supplied with blood. In this embodiment the sheet material of the seal need not have a preformed curvature in the width direction, when the flexible sheet material is sufficiently flexible to conform to the curvature of the wall of the vessel. However for easy retrieval and increased sealing properties, a preformed curvature in the width direction is preferred.

Conclusion: In the porcine carotid and coronary artery, insertion or retrieval of the seal according to the present invention required less than 30 seconds. Once properly positioned, the seal provided a bloodless arteriotomy for precise (microsurgical) end-to-side anastomosis suturing without interfering with recipient artery blood flow.

Figure 12A:
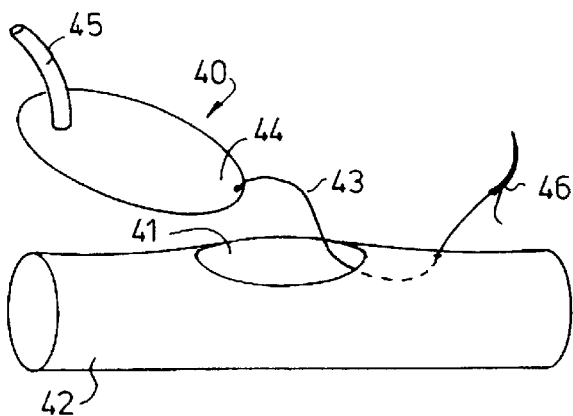
FIGS. 12a–12c show an embodiment of a sealing device having a suture wire connected to its forwards part.
Figure 12B:
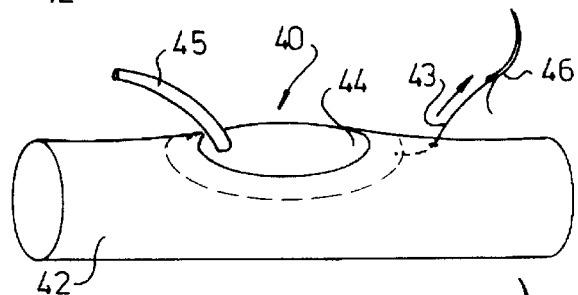
Figure 12C:
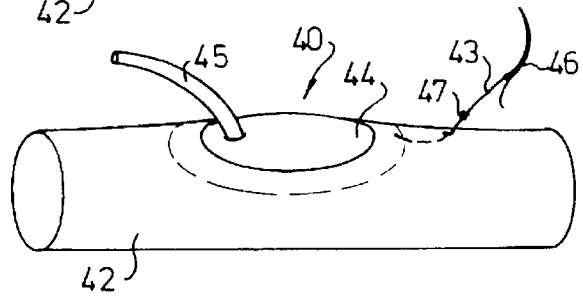

FIGS. 12a to 12c show a construction by which introduction of the temporary arteriotomy seal 40 into the arteriotomy 41 of an artery 42 is facilitated. A suture wire 43 is connected to the forward part 44 of the seal 40. A needle 46 is connected to the end of suture wire 43. By carefully pulling the suture wire 43, the seal 40 is drawn into the arteriotomy 41 where it unfolds. By simultaneously pulling at the suture wire 43 and at the gripping element 45, a proper positioning of the seal 40 in the mid line is facilitated. During anastomosis suturing, complete ejection of the seal 40 out of the arteriotomy 41 can be prevented by tying a knot 47 in the suture wire 43 close to its exit point as shown in FIG. 12c. Prior to removal of the seal 40 from the artery 42, the needle 46 and the knot 47 are removed by cutting the suture wire 43.

Figure 13A:
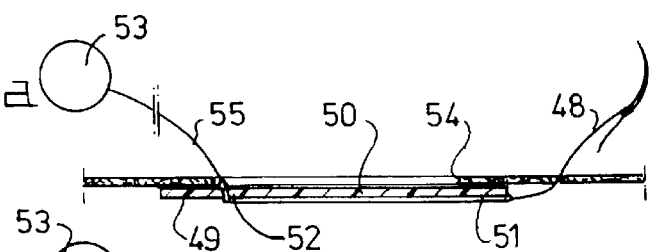
FIGS. 13a–13c show an embodiment wherein a suture wire extends along the lower side of the sealing device.
Figure 13B:
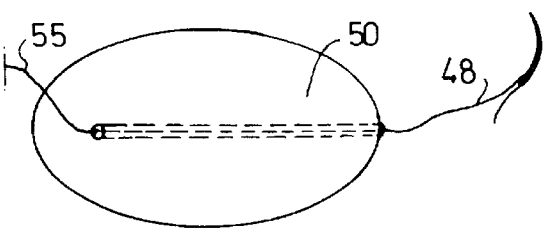
Figure 13C:
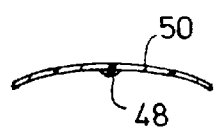

FIGS. 13a–13c show a construction wherein the suture wire 48 extends along the lower side 49 of a seal 50 from the forward part 51 to a rearward part 52. The suture wire 48 is connected to the seal 50 by means of a suitable adhesive. At the rearward part 52, the wire 48 penetrates the sheet material of the seal and extends towards a blocking and gripping device 53 which is attached to the end of the rearward part 55 of the suture wire 48. The blocking and gripping device 53 is not drawn to scale but will generally have a larger diameter than the arteriotomy 45 for preventing "upstream" dislodgement of the seal into the artery in case of retrograde blood flow. This embodiment allows the seal to be tightly rolled-up so that it can be placed inside a jacket which has a tapering form, more or less like "an umbrella case". Once rolled-up, the jacket with the seal may be placed within the vessel by means of the suture wire 48 without the use of a separate introducer. At the side of the toe of the seal the jacket may be withdrawn from the vessel maintaining the tension on the suture wire and avoiding the seal to be pulled back. In this construction the seal should easily slide from its jacket, which can be achieved by using the same material for the jacket and the seal preferably comprising a liquid layer therebetween. Furthermore the seal does not adhere to itself in the rolled-up position.

FIGS. 14a and 14b show an embodiment wherein a flexible and deformable material 56 is placed on the upper side 57 of the seal around a closed contour. The flexible and deformable material 56 is for instance made of hydrogel and improves sealing against an irregular surface of the wall 58 of the artery which may have irregularities due to arteriosclerosis.

FIGS. 15a and 15b show an embodiment of an introducer 60 for introducing a rolled-up sealing device into the arteriotomy. The introducer 60 comprises a handle 61 and shaft 62 at the end of which a cylindrical sleeve 63 is connected. The sleeve 63 comprises an extension 64 comparable to a shoe horn which can be locked into the arteriotomy upon introducing the rolled up sealing element. The sealing element will be placed in a rolled-up position inside the sleeve 63. Once the introducer 63, 64 is in place in the arteriotomy, the seal is pushed through the introducer into the artery, while the introducer is withdrawn from the arteriotomy.

Figure 16:
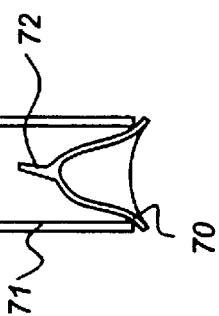
FIGS. 16a–16c show a schematic side view of a method of folding the sealing device according to the present invention along its width direction.
Figure 16:
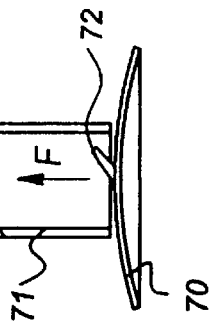
Figure 16:
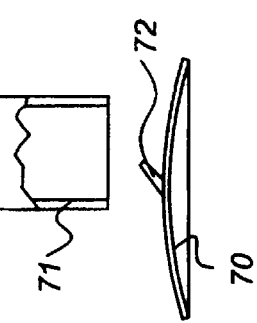

FIGS. 16a–16c show three subsequent steps of placing a flexible sealing device 70 according to the present invention inside the tube of an introducer by grabbing the gripping element 72 and pulling the sealing device 70 upwardly inside the tube 71 by exerting an upward force in the direction of the arrow F on the gripping element 72. By this operation the sealing element 70 is folded along its width direction W.

Figure 17:
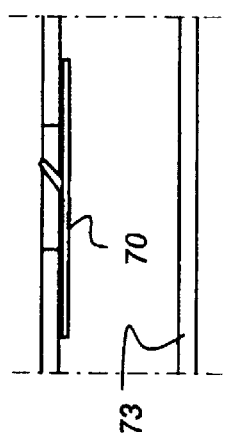
FIGS. 17a–17c show the introduction of the folded sealing device of FIGS. 16a–16c into an arteriotomy.
Figure 17:
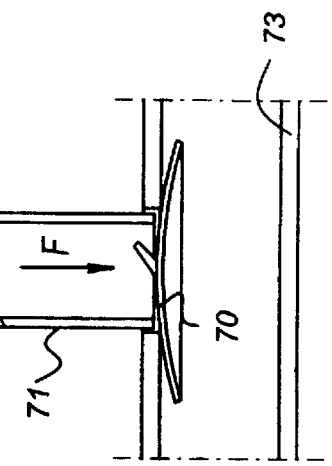
Figure 17:
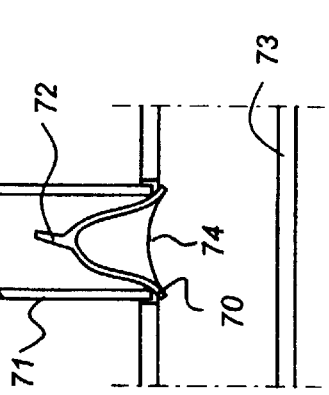

FIGS. 17a–17c show the introduction of the sealing device 70 into a vessel or artery 73 by placing the end part of the tube 71 into the opening or arteriotomy 74 and by lowering the gripping element 72. Hereby the sealing device 70 unfolds to assume its extended length dimension within the vessel 73 such that the arteriotomy 74 is sealed and the tube 71 can be removed. In this operation the introducer pen forms the following functions:

1. taking hold of sealing device 70
2. folding the sealing device 70
3. manipulating the vessel wall, for manoeuvring the sealing device above the arteriotomy,
4. atraumatic entrance inside the ateriotomy,
5. atraumatic depositioning of the sealing device into the artery and allowing the sealing device to unfold and
6. release of the sealing device.

The present method and introducer device allow an almost perpendicular approach of the introducer to the arteriotomy. Secondly, because the introducer is able to grasp the gripping element 72 repeatedly, it permits the sealing device to be relocated by the introducer once it has entered into the vessel 73. The above properties render the introducer and the method of application of the sealing device according to FIGS. 17a–17c particularly suitable to function in a closed chest environment.

Furthermore, the introducer tube as shown in FIGS. 16a–16c and 17a–17c allows the sealing device 70 to be introduced single handedly. Furthermore, the arteriotomy required to insert the sealing device 70 can remain small. The present embodiment allows adaptation of the tube 71 to an endoscopic instrument wherein different additional instruments may be comprised in the tube such as an arteriotomy knife, light carrying fibres for elumination purposes, endoscopic fibre bundles for increased vision, flush and suction channels and the like.

Figure 18:
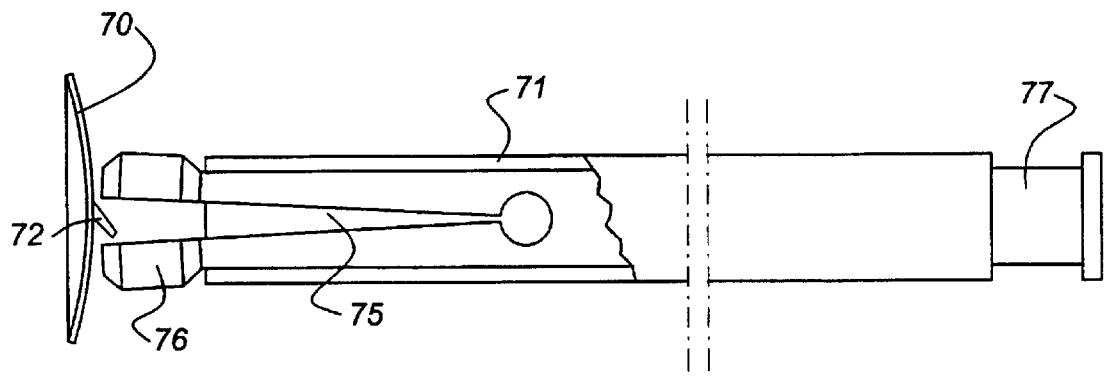
FIGS. 18a and 18b show an introducer comprising a gripper head in its engaging and in its retracted position, respectively.
Figure 18:
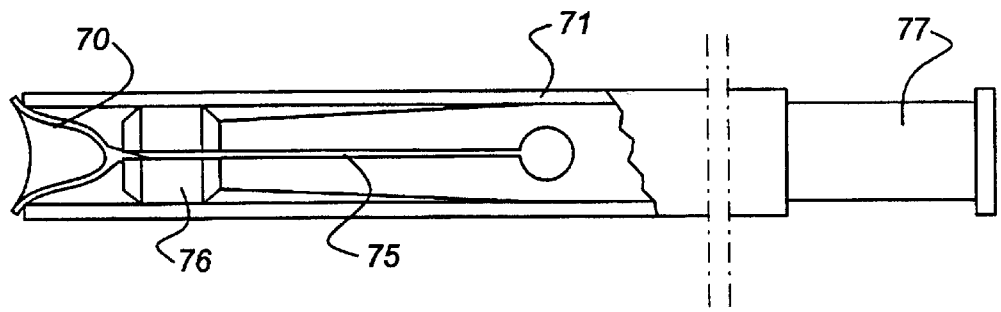

FIG. 18a shows an introducer having a tube 71 and displaceable therein a gripping device 75. The gripping device comprises a gripper head 76 having two flexible clamping elements defining a slit therebetween, in which slit the gripping element 72 of the sealing device 70 can be placed. The upper end of the introducer comprises a pull rod 77 for retracting the gripper head 76 within the tube 71. As shown in FIG. 18b, the flexible clamping elements of the gripper head 76 are pressed together when the gripper head is retracted within the tube, such that the gripping element 72 of the sealing device 70 is clamped therebetween. Retraction of the gripper head 76 inside the tube 71 causes the sealing device 70 to be folded along its width direction W. Thereafter it can be introduced into the arteriotomy in the manner as shown in FIGS. 17a–17c.

Figure 19:
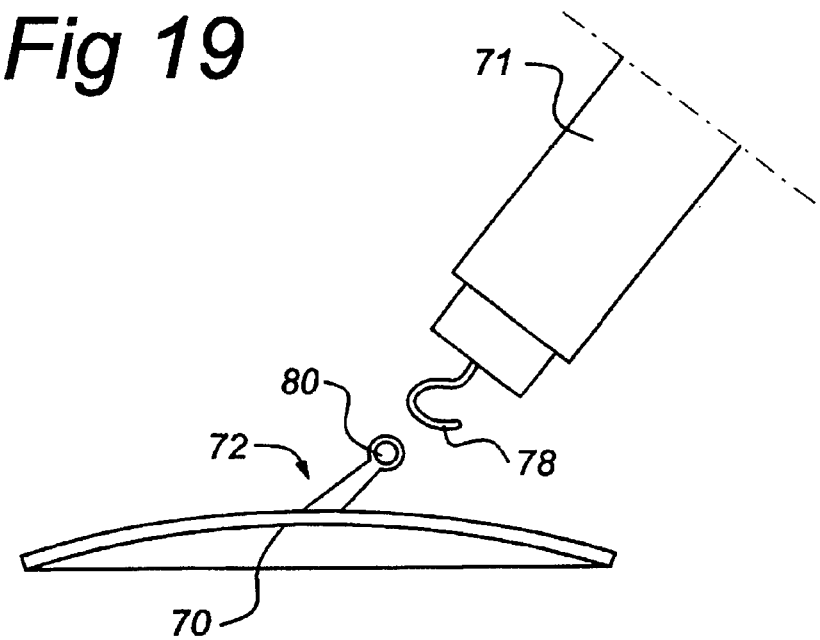
FIG. 19 shows an embodiment wherein the engagement means on the sealing device comprise an eye, the gripper head of the introducer comprising a retractable hook.

FIG. 19 shows an embodiment wherein the gripper head of the introducer comprises a retractable hook 78. The hook can engage with an eye 80 on the gripping element 72 of the sealing device 70.

Figure 20:
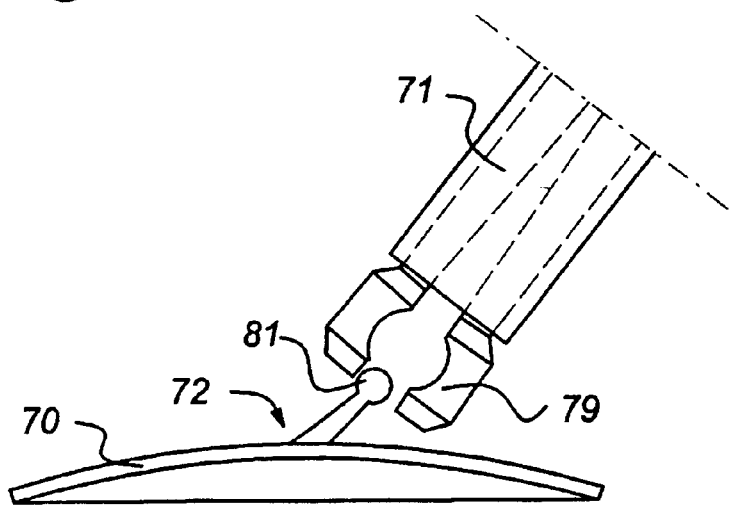
FIG. 20 shows an embodiment wherein the engagement means on the sealing device comprise a bulbous end part, the gripper head of the introducer comprising flexible tongues.

In the embodiment shown in FIG. 20, the introducer comprises two flexible tongues 79 which can engage around a bulbous protrusion 81 at the end of the gripping element 72 of the sealing device 70.

What is claimed is:

1. Medical device (1,19,26') for insertion into a blood vessel through an opening in a wall of said vessel, the device comprising:
    an elongated flexible sheet material (2,32) having a length dimension (L) and a width dimension (W), the sheet material (2,32) being foldable in the width direction for placing the sheet material into an insertion configuration and the sheet material being unfoldable to assume a sealing configuration inside the blood vessel for contacting the blood vessel wall in a sealing manner, the sheet material in the sealing configuration extending along an open contour, conforming to and partly covering an interior surface of the blood vessel wall;
    a gripping element (3,31) on an outer surface of said sheet material;
    wherein the flexible sheet material (2,32) in an untensioned state is curled in the width direction, wherein the sheet material folds in the width direction (W) upon exertion of a pulling force on the gripping element (3,31), directed generally in the length direction, and upon contacting of the sheet material by the sides of the opening in the vessel wall after partially closing the opening.

2. Medical device (1) according to claim 1, wherein the gripping element (3) is placed offset from the midpoint of the length dimension (L) at a predetermined angle (α) with respect to the outer surface of the flexible sheet material (2), the gripping element (3) being inclined towards a shorter part of the length dimension (L).

3. Medical device (19) according to claim 1, wherein the flexible sheet material comprises an inflatable body (22,23, 26) and a supply duct (24) for supply of a fluid into the inflatable body (22,23,26).

4. Medical device (19) according to claim
    wherein the flexible sheet material comprises two membranes (22,23) that are sealingly connected along their perimeter (25) and a supply duct (24) for supply of a fluid into the space between the membranes (22,23).

5. Medical device (26') according to claim 1, wherein the gripping element (31) is formed by a supply duct which ends in an opening (27) in the flexible sheet material (32) for administration of substances through the supply duct into a blood vessel.

6. Medical device (1,19,26') according to claim 1, wherein the flexible sheet material (2,32) is thinner near a perimeter of the flexible sheet material than near a center of the sheet material.

7. Medical device (1,19,26') according to claim 1, wherein the gripping element comprises an upstanding ridge (3').

8. Medical device (1,9,26') according to claim 1, further comprising orientation markings on the outer surface.

9. Medical device (1,19,26') according to claim 1, wherein a stiffness of the flexible sheet material (2,32) in a length direction is larger than a stiffness in a width direction.

10. Medical device (1,19,26') according to claim 1, wherein the flexible sheet material is non biodegradable.

11. Medical device according to claim 1, comprising a suture wire (43,48) connected to a forward part (44,51) of the sheet material.

12. Medical device according to claim 11, wherein a needle (46) is connected to the suture wire.

13. Medical device according to claim 11, wherein the suture wire (48) extends from a forward part (51) to a rearward part (52) of the sheet material along a lower side (49) thereof, and penetrates the sheet material at the rearward part (52) to continue at an upper side thereof (55).

14. Medical device according to claim 13, wherein the suture wire (48) is adhesively connected to the lower side (49).

15. Medical device according to claim 13, wherein a blocking and gripping device (53) is connected to an end of the suture wire (55) at the rearward part (52) of the sheet material.

16. Medical device according to claim 1, wherein the sheet material is at its upper surface (57) at or near its perimeter provided with an easily deformable sealing material (56).

17. Medical device according to claim 1, wherein the gripping element (72) comprises engagement means (80, 81) for engaging with a gripper device (78,79).

18. Medical device according to claim 17, wherein the engagement means comprise a bulbous part (81) on the gripping element (72).

19. Medical device according to claim 17, wherein the engagement means comprise a hook or an eye (80) on the end of the gripping element (72).

20. Assembly comprising a medical device according to claim 1 and an introducer (60), wherein the introducer (60) comprises a generally cylindrical receptor (63) having a tapering wall extension (64) for locking into an arteriotomy.

21. Assembly comprising a medical device according to claim 1 and an introducer, wherein the introducer comprises a tube (71) and a gripper device (75) displaceable in the length direction of the tube, the gripper device having a gripper head (76) which is adapted to engage with the gripping element (72) of the medical device (70).

22. Assembly according to claim 21, wherein the gripper head (76) has two flexible parts defining a slit therebetween, the flexible parts, upon retracting the gripper head within the tube, engaging with a wall of the tube such that the slit is narrowed.

23. Assembly according to claim 21, wherein the gripper head comprises a hook element (78).

24. A temporary seal for an opening in a blood vessel, comprising:
  a sheet of flexible material that has a generally oval peripheral edge with a length greater than a width, said sheet having lateral sides that curl towards one another so that said sheet is part of a cylinder in an untensioned state,
  a convex outer surface of said sheet being structured and arranged to conform to an interior surface of a blood vessel completely around a periphery of an opening in the blood vessel when the temporary seal is inserted through the opening; and
  a gripping element attached to said convex outer surface and that is structured and arranged to withdraw said sheet from the blood vessel when said gripping element is pulled away from the opening.

25. The seal of claim 24, wherein said gripping element is L-shaped and comprises a vertical arm whose height is greater than its length and a horizontal ridge whose height is less than its length, said horizontal ridge being joined to said vertical arm.

26. The seal of claim 24, wherein said lateral sides of said sheet touch each other in the untensioned stated.

27. The seal of claim 25, wherein said sheet is hollow and uncurls when tensioned by inflation.

28. The seal of claim 27, wherein one said lateral side of said sheet is more compliant than the other said lateral side of said sheet.

29. The seal of claim 24, wherein said sheet comprises two separate hollow portions on opposite said lateral sides that are separately inflatable, and an opening through said sheet between said hollow portions.

30. The seal of claim 24, further comprising an inflatable donut completely around a periphery of said convex outer surface of said sheet and that conforms to the interior surface of a blood vessel completely around the periphery of the opening.

* * * * *